United States Patent [19]

Cigaina

[11] Patent Number: 5,423,872
[45] Date of Patent: Jun. 13, 1995

[54] PROCESS AND DEVICE FOR TREATING OBESITY AND SYNDROMES RELATED TO MOTOR DISORDERS OF THE STOMACH OF A PATIENT

[76] Inventor: Valerio Cigaina, Via 4 Novembre 3a, 31050 Villorba (Treviso), Italy

[21] Appl. No.: 67,390

[22] Filed: May 26, 1993

[30] Foreign Application Priority Data

May 29, 1992 [IT] Italy .................................. MI92A1325

[51] Int. Cl.⁶ ............................................... A61N 1/05
[52] U.S. Cl. ........................................ 607/40; 607/133
[58] Field of Search .................... 607/133, 72, 116, 40, 607/126, 128, 9

[56] References Cited

U.S. PATENT DOCUMENTS

| | | | |
|---|---|---|---|
| 3,411,507 | 11/1968 | Wingrove | 607/40 |
| 5,133,350 | 7/1992 | Duffin | 607/9 |
| 5,179,962 | 1/1993 | Dutcher et al. | 607/128 |
| 5,188,104 | 2/1993 | Wernicke et al. | 607/40 |

Primary Examiner—William E. Kamm
Assistant Examiner—Scott M. Getzow
Attorney, Agent, or Firm—Herbert Dubno

[57] ABSTRACT

The process for treating obesity and syndromes related to motor disorders of the stomach of a patient consists in artificially altering, by means of sequential electrical pulses and for preset periods of time, the natural gastric motility of the patient to prevent emptying or to slow down gastric transit.

15 Claims, 2 Drawing Sheets

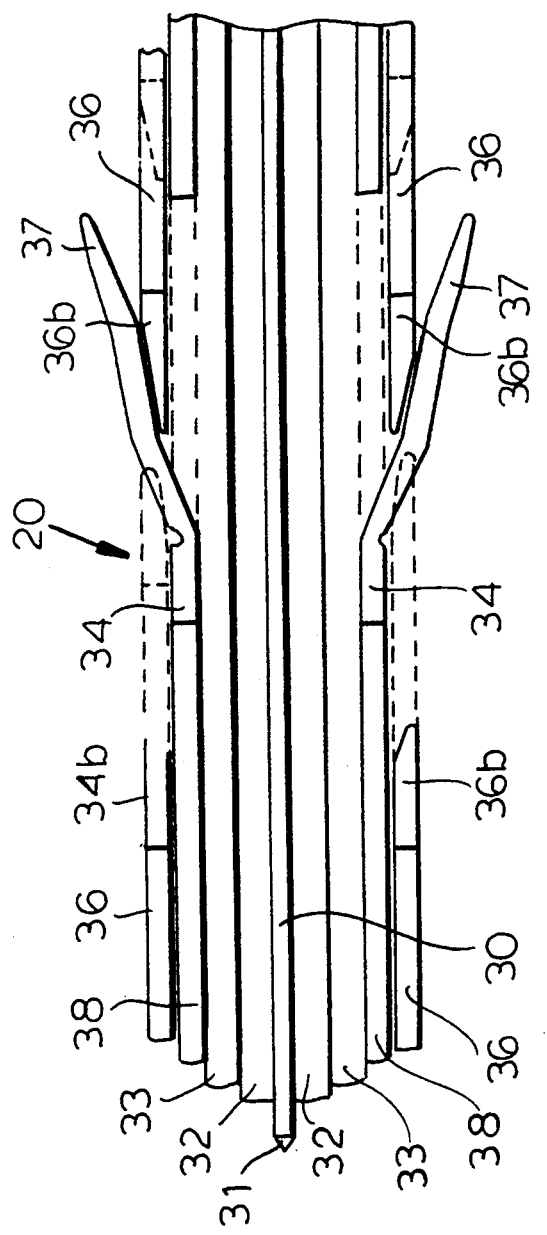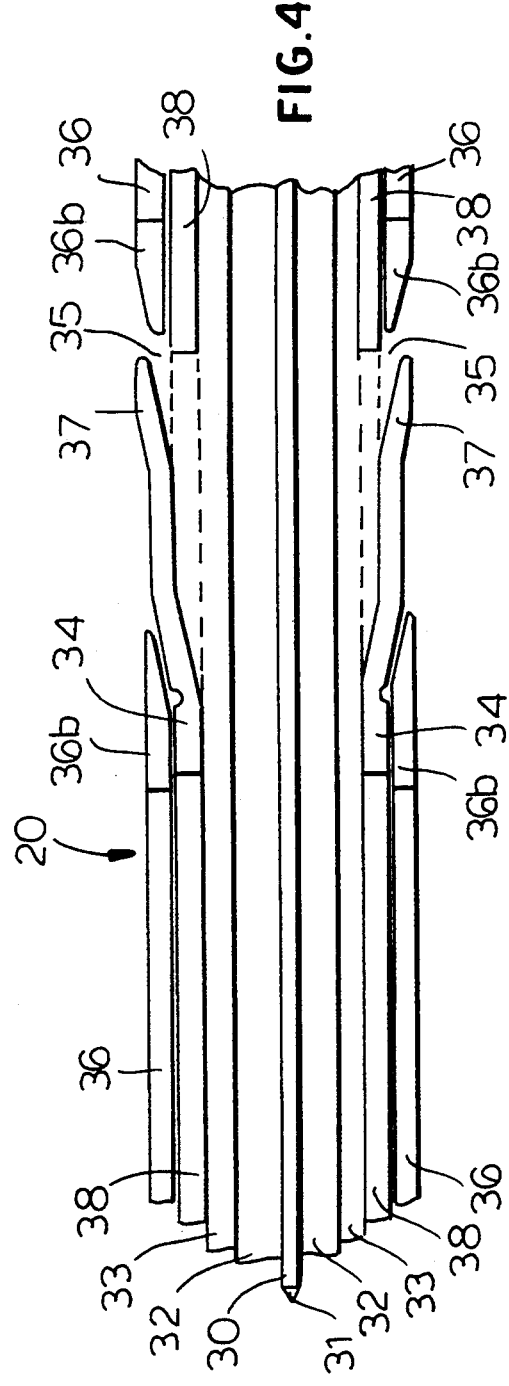

PROCESS AND DEVICE FOR TREATING OBESITY AND SYNDROMES RELATED TO MOTOR DISORDERS OF THE STOMACH OF A PATIENT

The present invention relates to a process and to a device for treating obesity and syndromes related to motor disorders of the stomach of a patient. As is known, the treatment of obesity related to hyperalimentation, i.e. to a subject who introduces food in excess of his actual caloric requirements (energy expenditure related to motor activity, work, environmental activity, etc.) is based on psychotherapeutic, pharmacological or dietary provisions or, in selected cases (pathogenic obesity), on surgical provisions.

BACKGROUND OF THE INVENTION

The modern surgical orientation (surgery is the only therapy that ensures real results in patients who have exceeded obesity values close to, or in excess of, 40 BMI, i.e. the ratio of weight to the square of the height) entails the reduction of gastric compliance, with the aim of limiting the subject's ability to ingest food, or of reducing the food absorption surface by shortening or bypassing part of the digestive canal; both aims are sought in some surgical procedures.

All of the surgical procedures currently in use have some immediate and/or delayed risks and surgery must thus be considered as an extreme solution.

Furthermore, even surgical treatment fails sometimes, since the patient becomes obese in or the complications are such as to force the surgeon to restore the original anatomical situation, with the consequence of failing to achieve the intended aim of reaching the ideal weight.

OBJECTS OF THE INVENTION

The primary aim of the present invention is to provide a process for treating obesity and to avoid the drawbacks of a highly invasive surgical technique.

Still another object is to provide the process achieving a more correct and functional nutritional pattern, preventing the emptying of the stomach or slowing down the transit of gastric content;

Yet another object is to provide the process which by means of different gastric visceral placements of the connecting means allows to treat syndromes related to motor disorders of the stomach, such as duodenogastric and gastroesophageal refluxes and relapsing duodenal peptic disorders (ulcer or phlogosis); and A further object of the present invention is to provide the process for treating obesity and syndromes related to motor disorders of the stomach of a patient which can also be used for outpatients since they do not use current surgical techniques.

Finally another object of the present invention is to provide an apparatus implementing the process.

SUMMARY OF THE INVENTION

These objects and others are substantially achieved by a process for treating obesity and syndromes related to motor disorders of the stomach of a patient and comprising the steps of artificially altering, by means of sequential electrical pulses and for preset periods of time, a natural gastric motility of the patient to prevent emptying or to slow down food transit.

This process is performed with a device for treating obesity and syndromes related to motor disorders of the stomach of a patient, characterized in that it includes an electrical stimulator which is provided with a means for connecting it at the level of the distal gastric antrum of the patient by laparoscopic means, the stimulator having an operating frequency comprised between 2 and 15 pulses per minute, in order to eliminate or reduce the motility of the stomach, so as to slow down or prevent gastric transit therein and/or improve the functionality of the lower esophageal and pyloric sphincters for a preset time.

BRIEF DESCRIPTION OF THE DRAWING

The above and other objects, features, and advantages will become more readily apparent from the following description, reference being made to the accompanying drawing in which:

FIGS. 3 and 4 are longitudinal sectional views of two different embodiment of the electrocatheter according to the invention.

SPECIFIC DESCRIPTIONS

Figure 1:
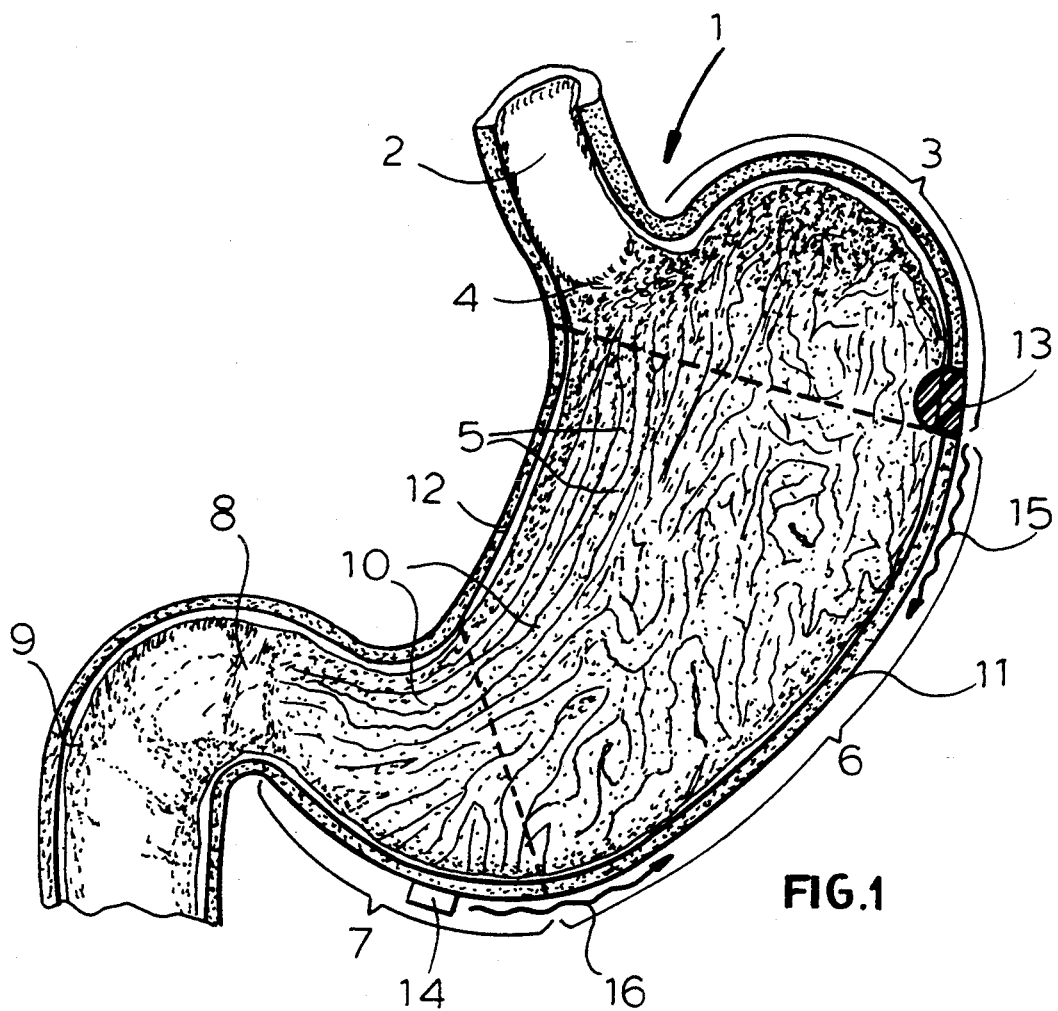
FIG. 1 is a sectional view of a stomach showing the device of the invention in place.

In order to further clarify the process and device for treating obesity and syndromes related to motor disorders of the stomach of a patient, according to the invention, the motor physiology of the gastric viscus is briefly described.

The stomach 1 is supplied by the esophagus 2, and has the fundus ventriculi 3, the cardia 4, a gastric canal 5, the corpus ventriculi 6, the antrum of the stomach, the pylorus 8, the duodenum 9 and mucous folds 10.

As is known, the stomach is divided into two parts as regards its motility: the fundus ventriculi 3, which has tonic wall movements, and the central part or corpus 6, which is characterized by phasic activity. Propulsive gastric movements begin at a point proximate to the greater curvature which is not clearly identified anatomically and is termed "gastric pacemaker".

The "gastric pacemaker" 13 sends electrical pulses (depolarization potential) approximately three times per minute; these pulses spread in an anterograde direction along the entire stomach in the form of waves 15 which have a sinusoidal shape.

The antrum 7 of the stomach has a continuous phasic activity which has the purpose of mixing the food which is present in the stomach. The passage of food into the duodenum 9 is therefore the result of a motility which is coordinated among the antrum 7, the pylorus 8 and the duodenum 9. To put it more simply, when the food has passed through the esophagus 2 it reaches the stomach.

The "gastric pacemaker" 13 spontaneously and naturally generates sinusoidal waves 15 along; the entire stomach; these waves allow the antrum 7, with movements which are coordinated together with those of the pylorus 8 and the duodenum 9, to make the food pass into the subsequent portions of the alimentary canal.

Now that the known physiology of the gastric motility of a mammal, such as a human being, has been established, the process according to the invention consists in artificially altering, by means of sequential electrical pulses and for preset periods of time, the natural gastric motility of a patient and/or the time and manner of contraction of the lower esophageal and pyloric sphincters to prevent emptying or slow down gastric transit or (both occurrences) prevent duodenal acidification during interdigestive phases or to prevent gastric reflux in the last portion of the esophagus.

Figure 2:
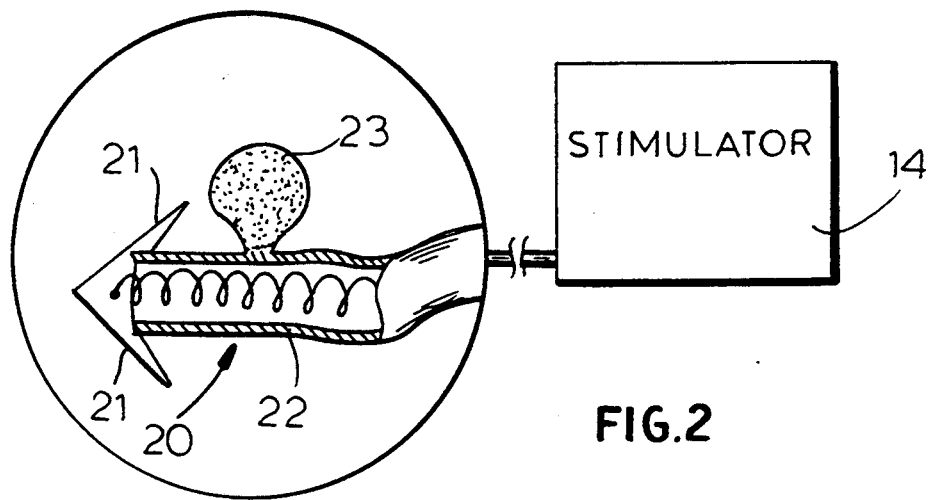
FIG. 2 is a schematic lateral elevation view of the terminal of the electrocatheter, or a means for connecting the electrical stimulator, shown in longitudinal cross-section.

More particularly, the sequential electrical pulses are generated by an electrical stimulator which includes an electrocatheter 20 (FIG. 2) which is applied by laparoscopic means to a portion of the seromuscular layer of the stomach of the patient (terminal of the electrocatheter on the antrum 14). In this manner, the electrical stimulus generates, along the entire stomach 1, one or more sinusoidal waves 16 which start in the gastric antrum and add, more or less synchronously, with those which correspond to the natural electrical activity of the stomach when emptying procedures are activated in the stomach.

In other words, the electrical stimulator induces in the stomach a motor incoordination (so-called antral tachygastria) in order to slow down or even prevent gastric transit through the pylorus into the intestine located downstream and thus allow treatment of obesity related to hyperalimentation or to modulate fasting gastric hypermotility for the treatment of relapsing duodenal ulcer in anxious subjects, or improve the functionality of the lower esophageal and/or pyloric sphincters in treating reflux esophagitis and gastropathy induced by duodenogastric reflux.

Therefore, the electrical stimulator, according to the motor phenomenon to be corrected (induction of antral tachygastria in obesity, modulation of gastric hypermotility in anxious subjects, increase in sphincter function in reflux disorders), has a purpose-specific and potentially patient-specific frequency, intensity, duration and period of stimulation, in addition to having a specific gastric location for the tip of the electrocatheter according to the type of disorder.

The stimulator can be programmed both for continuous stimulation and for "on demand" stimulation, i.e. at the onset of a particular electrical activity which can be detected by the stimulator itself through the electrocatheter.

Furthermore, the electrical stimulator, in order to allow to perform iatrogenic tachygastria, has a preset operating frequency and period which may obviously vary according to the alteration of stomach motility to be obtained and/or to the pathological condition of the patient.

More precisely, the electrical stimulator 14 has an operating frequency comprised between 2 and 15 pulses per minute. Considering that the natural pacemaker 13 is subject to electrical depolarization approximately three times per minute, and that this depolarization is transmitted with an anterograde direction in the entire viscus, the electrical stimulator must have an operating frequency substantially close to, and/or higher than, three pulses per minute. Each one of these electrical pulses has a duration comprised between 10 and 90 milliseconds and in particular a duration of 50 milliseconds.

The electrical discharge of each pulse can vary from approximately 1 to 5 volts (voltage-controlled stimulation) and from 2 to 15 milliamperes with constant current. Conveniently, the electrocatheter 20 can be applied in the distal portion of the antrum even on outpatients, since this portion is easily visible during laparoscopy.

As shown, therefore, in order to produce antral tachygastria for limited intervals within a 24-hour period, and prevent or slow down stomach emptying, the viscus of the patient is stimulated electrically as described above.

In this case, the obese patient may use his normal gastric motor activity only when electrical stimulation ceases.

Since water requires no digestive process and produces no peristaltic activity (an experimental finding), it can pass from the stomach into the duodenum (short operating intervals of the electrical stimulator can be used to facilitate this transit).

The device for treating obesity and syndromes related to motor disorders of the stomach of a patient, as described, includes an electrical stimulator which is appropriately located subcutaneously in the abdominal wall, is anchored to the fascia of the musculus rectus abdominis, and is connected to the distal gastric antrum by means of an electrocatheter 20 the terminal portion thereof of which is provided with metallic micro-barbs 21, for example two, which are angled so as to allow application of the tip of the catheter and prevent its extraction. For this purpose, the remaining portion of the electrocatheter is covered by a sheath 22 made of inert and biocompatible plastic material which has, in the part proximate to its tip, a small expansion 23 with a non-uniform velveted surface for anchoring with a stitch in order to ensure lasting adhesion of the electrocatheter to the viscus. The rough surface of the expansion 23 has the purpose of producing a fibrous reaction of the gastric serosa, contributing to the firmness of the anchoring.

In a different embodiment, the electrocatheter 20 is provided with a terminal portion having a reversible and non-traumatic anchoring system, as shown in FIGS. 3 and 4.

For this purpose, the entire electrocatheter is covered by a second sheath, made of inert and biocompatible plastic material, which allows its application even during the diagnostic phase, since the anchoring can be reversible and the electrocatheter is therefore removable.

The expression "diagnostic phase" designates electromyographic study of the viscera with application of visceral electrocatheters in a monopolar system.

As is shown in FIG. 3, the electrocatheter 20 has a stimulating conductor 30 which is provided with a tip 31 and is covered by a first insulating sheath 32.

A second insulating sheath 33, made of flexible metallic material (spiral spring), forms the return conductor of the electrocatheter.

A ferrule 34 is fitted on the second sheath 33 and is provided with laminas which can move and retract and are elastically resilient so that they can protrude through openings or slots 35 formed on a flexible tubular slider 36 (spiral spring) which is suitable, by means of a rigid cylinder 36b provided with inclined planes, to move the laminas into a divaricated or closed position with respect to the axis of the stimulating conducting wire by means of its translatory motion along the catheter body.

These laminas are the means for the electrical connection of the return conducting wire, which is thus in contact, like the stimulating conducting wire, with the tissues of the sub-serosal layer of the gastric wall. The metallic ferrule 34 continues, with the same diameter, by means of the insulation 38 along the entire length of the catheter.

In particular, the laminas have ends 37 which are inclined to allow engagement with the slider 36.

For the application of the electrocatheter 20 it is desirable to first produce a wheal with physiological solution and cortisone on the serosal surface of the stomach, in order to avoid unwanted perforation of the viscus, limit the insertion of the tip of the catheter to the sub-serosal layer of the viscus, and reduce tissue impedance.

The operating parameters of the device can be adjusted with an external programmer, and the electrical stimulator can be activated and/or deactivated with a magnet, as for example with medullary stimulators.

The invention achieves the intended aim and objects and achieves numerous important advantages.

A process and a device for treating obesity and syndromes related to motor disorders of the stomach of a patient have in fact been provided which avoid many of the drawbacks and contraindications of current operations, which are designed to change alimentary physiology by altering the normal anatomy of a patient.

Furthermore, the process is not particularly difficult to perform, since a simple operative laparoscopy allows endoabdominal application of an electrocatheter and a simple surgical maneuver allows the implantation of an electrical stimulator on the surface of the abdominal wall, particularly anchored on the fascia of the musculus rectus abdominis.

The invasiveness of the procedure always remains considerably less than that of a bariatric operation.

It is furthermore stressed that the:possibility of altering gastric motility with electrical stimulations implies that the device is applicable in disorders such as relapsing peptic duodenal ulcer of anxious subjects, gastric peptic disorders induced by duodenogastric reflux, and esophageal peptic disorders induced by gastroesophageal reflux.

As regards the first disorder, if we consider that duodenal ulcer is the consequence of an alteration in gastric motility which leads to acidification of the duodenum caused by the emptying of gastric juice into the duodenum during interdigestive phases, this disorder can be treated by inducing antral tachygastria in response to a pathological increase in the frequency induced by the natural pacesetter, which is typical of the anxious condition, thus slowing down a hyperperistalsis which is not required by any digestive process but is merely the consequence of a cortical conditioned reflex.

In this case, particular characteristics are provided for the electrocatheter and for its placement, in addition to a different programming of the electrical stimulator, which will have to act in response to a particular recorded electrical activity.

The electrocatheter, which is always appropriately sheathed, is placed so that it has three points of seromuscular contact (on the longitudinal line) and thus also three openings or slots with no sheath (two poles for the bipolar type and one pole for the monopolar type) for reception and/or stimulation: one on the greater curvature in the region of the natural pacesetter, and two in the antral region, so that both can receive and the bipolar one can stimulate. It is obvious that the insertion of the third pole requires a further flexible conductor similar to 33, an insulating sheath similar to 38 and a metallic ferrule to ensure contact of the third pole with the seromuscular layer.

The purpose to be accomplished is therefore to prevent the viscus from emptying its acid liquid during interdigestive phases into the duodenum, which is physiologically alkaline, in the same conditions: in order to achieve this purpose, pathological hyperperistalsis is stopped or slowed down by inducing, with an artificial ectopic pacemaker, an antral tachygastria during which it has been extensively demonstrated that no propulsive peristaltic movements are recorded.

For reflux disorders, the electrical stimulator is used during digestive rest phases, for example in the early hours of the morning during nocturnal rest, and is always appropriately programmed and designed for sphincter release at the onset of upstream peristaltic activity; this is done to avoid another disorder, such as esophageal achalasia.

The same principle holds for duodenogastric biliary reflux.

An electrocatheter with a recording point assesses electrical and/or mechanical activity by means of a monopolar terminal and/or a transducer of the muscular mechanical tension of the antrum, which acts as guide for the duration of the pyloric stimulation which is performed from a bipolar opening of the catheter.

The device thus conceived is susceptible to numerous modifications and variations, all of which are within the scope of the present inventive concept.

Furthermore, all the details may be replaced with technically equivalent elements. The materials employed, the shapes and the dimensions may be any according to the requirements.

I claim:

1. A process for treating obesity and syndromes related to motor disorders of the stomach of a patient, comprising the steps of:
    (a) mounting an electrical stimulator subcutaneously on the abdominal wall and anchoring the stimulator onto the fascia of the musculus rectus abdominis;
    (b) guiding an electrocatheter operatively connected with the stimulator along a path to place the electrocatheter in stomach wall tissue and to insert a tip of the electrocatheter in the seromuscular layer of the gastric antrum; and
    (c) generating sequential electrical pulses for a preset period of time by the electrical stimulator and transmitting the electrical pulses through the tip to the stomach to stimulate the entire stomach, thereby artificially altering a natural gastric motility of a patient to be treated to slow down food transit through the stomach.

2. The process defined in claim 1 wherein the pulses are in a form of sinusoidal waves propagated along the entire stomach, the sinusoidal waves generated by the electrical stimulator being identical to sinusoidal waves generated naturally by a gastric pacemaker of the stomach.

3. The process defined in claim 1 wherein the electrical pulses are generated at a preset operating frequency, the preset period of time being varied according to an individual characteristics of a patient to be treated.

4. The process defined in claim 3 wherein the preset operating frequency varies from 2 to 15 pulses per minute.

5. The process defined in claim 1 wherein each of the pulses has a duration between 10 and 90 milliseconds and corresponds to a specific chronaxie defining excitability threshold in terms of stimulus length.

6. The process defined in claim 1 wherein each of the pulses has a respective discharge varying from 1 to 10 volts and from 2 to 15 milliamperes DC according to electrical characteristics of the catheter and to a particular rheobase of a tissue to be stimulated.

7. The process defined in claim 1 wherein the step (b) includes placing the electrocatheter in the gastric parietal seat by using a laporascopic procedure.

8. The process define in claim 1 wherein the step (c) includes altering of a proper function of the lower esophageal, pyloric sphincters and the natural gastric motility of the patient to improve sphincter function and reflux disorders and to slow down gastric transit for preventing duodenal acidification caused by a faster interdigestive transit of a gastric juice.

9. A device for treating obesity and syndromes related to motor disorders of the stomach of a patient, the device comprising:
   an electrical stimulator adapted to be applied subcutaneously on the abdominal wall and generating an operating frequency including from 2 to 15 pulses per minute; and
   connecting means for operatively connecting the electrical stimulator with an area of the stomach of a patient to be treated, the connecting means comprising an electrocatheter guidable along an insertion direction and including:
      an elongated internal stimulating conductor formed with a metallic conducting free end adapted for transmitting the pulses at the operating frequency over the area of the stomach to be treated to artificially alter a natural gastric motility of the patient for preventing emptying or slowing down food transit, for improving functioning of the lower esophageal or pyloric sphincters and for preventing acidification of the duodenum for a preset time,
      a plurality of pointed but not sharp angled metallic barbs operatively connected with the conductor and spaced angularly from one another, the barbs extending in a direction opposite the direction of insertion for stabilizing contact between the electrocatheter and the viscus,
      the barbs extending radially outwardly from the conducting end of the stimulating conductor, and
      an insulating layer and with a flat velveted plastic expansion formed on a sheath and located proximate to the conducting end for anchoring the electrocatheter on the gastric serosa with a surgical stitch.

10. A device for treating obesity and syndromes related to motor disorders of the stomach of a patient, the device comprising:
   an electrical stimulator adapted to be applied subcutaneously on the abdominal wall and generating an operating frequency including from 2 to 15 pulses per minute; and
   connecting means for operatively connecting the electrical stimulator with an area of the stomach of a patient to be treated, the connecting means comprising an electrocatheter guidable along an insertion direction and including:
      an elongated internal stimulating conductor formed with a metallic conducting free end adapted for transmitting the pulses at the operating frequency over the area of the stomach to be treated to artificially alter a natural gastric motility of the patient for preventing emptying or slowing down food transit, for improving functioning of the lower esophageal or pyloric sphincters and for preventing acidification of the duodenum for a preset time,
      a plurality of pointed but not sharp angled metallic barbs operatively connected with the conductor and spaced angularly from one another, the barbs extending in a direction opposite the direction of insertion for stabilizing contact between the electrocatheter and the viscus,
      a return conductor surrounding the stimulating conductor and spaced therefrom,
      an insulating sheath between the stimulating and return conductors,
      a rigid cylinder mounted on opposite ends of the return conductor, the cylinder being provided with the plurality of barbs, the barbs being elastic laminas provided with respective free ends and divaricating from inserting to anchoring positions, and
      an insulating flexible tubular slider on the return conductor guidable therealong and provided with gripping means for engaging the laminas in the inserting position, the laminas spreading apart upon displacing of the slider to anchor the electrocatheter to the viscus.

11. The device defined in claim 10 wherein the gripping means includes a plurality of formations engaging respective free ends of the laminas in the inserting position, the free ends being inclined with respect to a peripheral surface of the catheter.

12. The device defined in claim 10 wherein the device is provided with control means for assessing electromechanical activity of a portion of the viscus in order to determine the sphincter stimulation time by means of a bipolar opening provided on the tubular slider.

13. The device defined in claim 12 wherein the control means includes a monopolar terminal or a transducer of muscular tension.

14. The device defined in claim 10 wherein the electrocatheter has up to three points of seromuscular contact, the gripping means including contact openings corresponding to the points for reception and/or stimulation of the stomach.

15. A process for treating obesity and motor disorders of the stomach of a patient which comprises:
   anchoring in tissue of the stomach at a location in a region of the antrum and on an outside of the stomach an electrode capable of producing an electrical wave propagatable over the stomach from the antrum; and
   periodically energizing said electrode with 2 to 15 pulses per minute at a voltage of 1 to 5 volts with a constant current of 2 to 15 milliamperes for a duration of 10 to 90 milliseconds to limit movement of food through the stomach.

* * * * *